United States Patent [19]

Ansuini et al.

[11] Patent Number: 4,780,664
[45] Date of Patent: Oct. 25, 1988

[54] CORROSION SENSOR FOR MEASURING THE CORROSION LOSS AND THE INSTANTANEOUS CORROSION RATE

[75] Inventors: Frank J. Ansuini, 29 Kennedy Blvd., Lincoln, R.I. 02865; Robert E. Howe, Londonderry, N.H.

[73] Assignee: Frank Asuini, Lincoln, R.I.

[21] Appl. No.: 917,715

[22] Filed: Oct. 10, 1986

[51] Int. Cl.$^4$ ............................................. G01R 27/02
[52] U.S. Cl. ............................ 324/65 CR; 324/65 R; 324/71.1; 324/71.2; 204/404
[58] Field of Search ............... 324/65 R, 65 CR, 71.1, 324/71.2; 204/1 T, 404, 147, 196

[56] References Cited

U.S. PATENT DOCUMENTS

| | | |
|---|---|---|
| 3,069,332 | 12/1962 | Seyl . |
| 3,078,707 | 2/1963 | Weaver . |
| 3,108,242 | 10/1963 | Scott, Jr. .................... 324/71.2 X |
| 3,124,771 | 3/1964 | Rohrback .................... 324/71.2 X |
| 3,197,724 | 7/1965 | Marsh . |
| 3,207,983 | 9/1965 | Schaschl et al. .................... 204/404 |
| 3,314,618 | 4/1967 | McDonald . |
| 3,357,237 | 12/1967 | Lebel . |
| 3,398,065 | 8/1968 | Marsh . |
| 3,406,101 | 10/1968 | Kilpatrick . |
| 3,486,996 | 12/1969 | Annand . |
| 3,578,409 | 5/1971 | Silverman . |
| 3,753,093 | 8/1973 | Gardner et al. .................. 324/65 R |
| 3,850,736 | 11/1974 | Seyl . |
| 4,140,990 | 2/1979 | Pompei Katz de Warrens .......................... 324/71.1 X |
| 4,294,667 | 10/1981 | Yamamoto et al. ................. 204/1 T |
| 4,326,164 | 4/1982 | Victor ............................ 324/65 CR |
| 4,380,763 | 4/1983 | Peart et al. ..................... 324/67 CR |
| 4,442,422 | 4/1984 | Murata et al. .................... 324/65 R |
| 4,454,006 | 6/1984 | Hausler et al. . |
| 4,455,530 | 6/1984 | Lee et al. ........................ 324/65 CR |
| 4,522,060 | 6/1985 | Murata et al. .................... 324/65 R |

FOREIGN PATENT DOCUMENTS

| | | |
|---|---|---|
| 2356242 | 11/1973 | Fed. Rep. of Germany . |
| 3007887.6 | 2/1980 | Fed. Rep. of Germany . |
| 2696868 | 11/1968 | Japan . |
| 1085871A | 1/1983 | U.S.S.R. . |

*Primary Examiner*—M. H. Paschall
*Assistant Examiner*—A. Jonathan Wysocki

[57] ABSTRACT

A corrosion sensor which is fabricated by photofabrication techniques in the form of two reduced size electrodes, which have wide and narrow areas so that both the instantaneous corrosion rate and the time averaged corrosion rate can be measured.

7 Claims, 2 Drawing Sheets

CORROSION SENSOR FOR MEASURING THE CORROSION LOSS AND THE INSTANTANEOUS CORROSION RATE

CROSS-REFERENCE TO RELATED APPLICATION

This application is related to U.S. Patent Application Ser. No. 817,061, filed Jan. 8, 1986 by the same inventors, and incorporated herein by reference.

BACKGROUND OF THE INVENTION

1. Field of the Invention

This invention relates to corrosion sensors, particularly those which measure instantaneous or cumulative corrosion rates.

2. Description of Related Art

There are several methods in the prior art of determining various corrosion rates. One method is called the weight-loss method, and it involves exposing accurately pre-weighed panels of materials to the particular environment whose corrosion rate is to be measured (e.g., the atmosphere or seawater). After being exposed for a lengthy period of time, usually ranging from one to twenty years, the panels are cleaned of any corrosive by-products which have accumulated and then reweighed to determine the amount of actual panel material which has been lost as a result of the corrosion. This provides a very accurate measure of the total corrosive loss, which is called the interval weight loss. This measurement is then used to try to obtain an average corrosion rate (weight loss per unit time).

Based on the amount of the weight loss, the time of exposure and several other factors, such as the amount of panel area exposed and the panel material density, an average corrosion rate is computed for the entire period. Unfortunately, the average corrosion rate computed from the weight loss measurement is not necessarily accurate. This is because it assumes that the corrosion rate has been constant during the long period involved. This is usually not true. Indeed, tests have indicated that the long term corrosion rates of certain alloys vary significantly over time. For example, the corrosion rate of steel in seawater actually decreases as the time of exposure increases.

The average corrosive rate computation based upon the long term weight loss measurement is also inaccurate for another reason. It assumes the environment being measured remains unchanged over the long period, when in reality the environment may exhibit both short and long term changes that significantly effect the corrosion rate. As a result, a long term weight-loss measurement often cannot be depended on as a basis for accurately determining either a specific short term corosion rate or the instantaneous corrosion rate at any given time. Similiarly, a short term weight loss measurement would not necessarily produce accurate information about long term corrosion. Accordingly, real-time monitoring of the actual instantaneous corrosion rate, along with a means to assess cumulative corrosion damage would be more useful.

The measurement of the instantaneous corrosion rate poses some problems. For example, in terms of atmospheric corrosion, that rate depends upon a number of factors, one of the most important of which is called time of wetness. Time of wetness sensors do exist in the prior art. They are called built-up sensors because they consist of a stack of metal plates separated from each other by an insulator, with alternate plates being electrically shunted. When the surfaces of the plates are wet, a small voltage is applied to them, and this results in a current flow between the plates. That current flow is proportional to the rate of corrosion actually occuring on the plates acting as the anodes. This generally indicates the severity of the corrosion occuring at the time. As a result, the instantaneous corrosion rate can be determined from this current by what is called a linear polarization resistance method ("LPR"). For small potential differences between the plates of the order of 10 mV or less, the resulting current will be proportional, based on what is called the polarization resistance. This resistance is inversely proportional to the natural corrosion rate of the plates. Accordingly, the current may be measured by means of a zero resistance ammeter and then converted to an instantaneous corrosion rate by means of Faraday's law.

There are several drawbacks to this. First, the instantaneous corrosion rate itself may vary by several orders of magnitude over a short time, and thus, the computed rate may or may not by itself produce much meaningful information. Secondly, these sensors are all hand made. This is not only time-consuming and expensive, but it also means that each sensor must be individually calibrated to allow for the inherent variations between the hand-made devices. Consequently, while this type of sensor is well suited for measuring short term corrosion or very low corrosion rates, it is not in widespread use because of its size (as a result of the stacked plates) and its cost.

Although the instantaneous corrosion rate is a useful measurement in some respects, another at least complimentary if not more meaningful corrosion rate is called the time averaged corrosion rate. It represents how much metal has been lost over a limited period of time. Generally, the time averaged rate of corrosion is determined by a method called the electrical resistance ("ER") method. In that method, the sensor comprises a long strip of metal which is exposed to the environment being measured. The corrosion will reduce the dimensions of the exposed strip, and as its thickness decreases, its electrical resistance will increase. This increase in the resistance can be converted into a time averaged corrosion rate, which is also a cumulative corrosion measurement.

The drawback of this ER type of sensor is its considerable bulk which is due to the long length of the exposed strip. Because of the small resistance involved, the strip must be long in order to make the initial resistance measureable. The alternative is to reduce the thickness of the strip. While such a reduction increases the resistance, it also shortens sensor life, as the strip will corrode entirely through in a shorter period of time.

As a result of all of this, there is a need for a corrosion sensor which is small, inexpensive to manufacture and is preferably capable of measuring the instantaneous corrosion rate as well as the time averaged corrosion rate.

SUMMARY OF THE INVENTION

We have discovered a new sensor, the new sensor being fabricated using photofabrication techniques in the form of at least two, reduced size electrodes, the electrodes, depending upon the electrical connections used, being able to apply the electrical resistance or linear polarization resistance techniques to determine both the instantaneous corrosion rate and the time averaged corrosion rate.

In the preferred embodiment, the sensor of this invention is fabricated by means of a photofabrication process in which thin steel foil is bonded to a thin backing to produce a laminate. The portion of the laminate with the exposed foil is covered with photoresist, and a photomask with the desired sensor pattern is applied. The laminate is then exposed to ultraviolet light, which exposes the unmasked portion of the photoresist. The exposed portion is removed in the usual manner, and the foil, which was under the exposed photoresist, is then etched away. This leaves the foil pattern under the mask, and the sensor is essentially complete once the unexposed photoresist is removed from the remaining foil.

The pattern of the foil in the preferred embodiment is unique. Essentially, it has two foil electrodes of equal area. Each has of a broad flat plate at each end. Each pair of plates are placed adjacent to each other with a small gap therebetween. The plates of each electrode are also connected together by a thin section. The thin sections are serpentined to save space and are referred to as resistive choke points. One of the choke points is shielded from the environment.

In operation, the instantaneous corrosion rate may be determined by linear polarization resistance techniques. The ends of each electrode are shunted, and a small bias voltage is applied between them. Because the resistance of the choke points will be so much higher than that of the plates, a current will flow between the corresponding plates, which act as the plates in the built-up sensor of the prior art. This current can be used to determine the instantaneous corrosion rate.

The time averaged corrosion rate is determined by using the electrical resistance method. As the resistance of the choke point is so much higher than that of the remainder of the electrodes, the resistance of the entire electrode, measured end-to-end, can be considered to be that of the choke point. The electrode with the choke point exposed to the environment is used for this purpose, with the other electrode with its protected choke point used for comparison purposes.

In another embodiment, a third electrode can be placed between the pairs of plates. In the case of environments with high resistivity, the normally low biasing voltage will be insufficient to produce a measurable current between the plates for the linear polarization method. In that case, the three electrode arrangement may be used to create a sufficient current flow. In this context, it is also possible to make the electrodes of different metals.

The sensors of this invention are inexpensive to make as well as small and compact. In addition, they permit the measurement of both the instantaneous corrosion rate and the time averaged corrosion rate at the same time.

BRIEF DESCRIPTION OF THE DRAWINGS

We turn now to a description of the preferred embodiment, after first briefly describing the drawings.

DESCRIPTION OF THE PREFERRED EMBODIMENT

Structure

Figure 1:
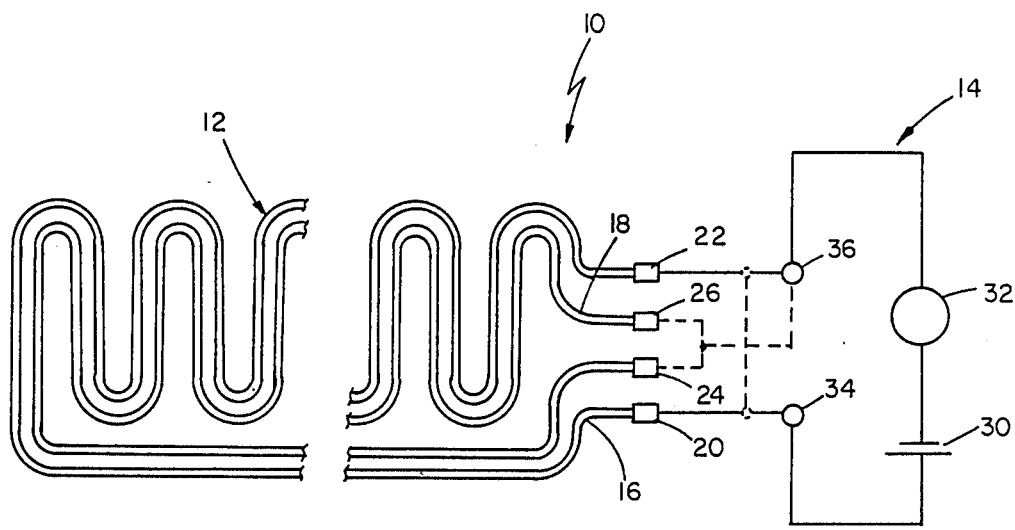
FIG. 1 is a simplified diagram of the corrosion sensor of this invention.

Referring to FIG. 1, a simplified diagram of the corrosion sensor of this invention is shown at 10. The sensor 10 is basically comprised of a sensing circuit 12 which is exposed to the environment to be measured, and an electrical source 14.

The sensing circuit 12 comprises a pair of electrodes 16, 18, each having a pair of electrical terminals. Electrode 16 has terminals 20, 22 (the outside terminals in the drawing). Electrode 18 has electrical terminals 24, 26 (the inside terminals in the drawing). The electrical source 14 is comprised of a voltage source 30 and a zero resistance ammeter 32 connected in series. There are also two terminals 34, 36 for the source 14.

Although this is a simplified version of the sensor of this invention, it does operate in the same general manner as that of the preferred embodiment described below and is useful in understanding the operation of the preferred sensor. The sensor 10 of FIG. 1 may be operated in two ways. First, the sensing circuit 12 is exposed to the environment for a length of time. Then if the time averaged corrosion rate is desired, terminals 20, 22 of electrode 16 are connected to the terminals 34, 36 of the electrical source 14, as shown by the solid lines. The current flow through the entire electrode 16 is then measured by the ammeter 32, and the resistance of the electrode is computed (the voltage of source 30 is known). As previously explained, the resistance will increase as the electrode corrodes away, and the measured resistance thus gives an indication of the amount of corrosion which has occurred over the particular period of time. The same measurement could, of course, be made using electrode 18.

To measure the instantaneous corrosion rate, both electrodes 16, 18 are connected to the electrical source. In particular, the terminals 22, 20 of electrode 16 are connected to terminal 34 of the electrical source 14, and terminals 26, 24 of electrode 18 are connected to terminal 36 of the source 14 (as shown by the dotted lines). The voltage applied here is small, in the order of 10 mV, but it creates a current flow between the electrodes 16, 18, which now act as plates. The ammeter 32 measures this current, which can then be used to determine an instantaneous corrosion rate.

Figure 2:
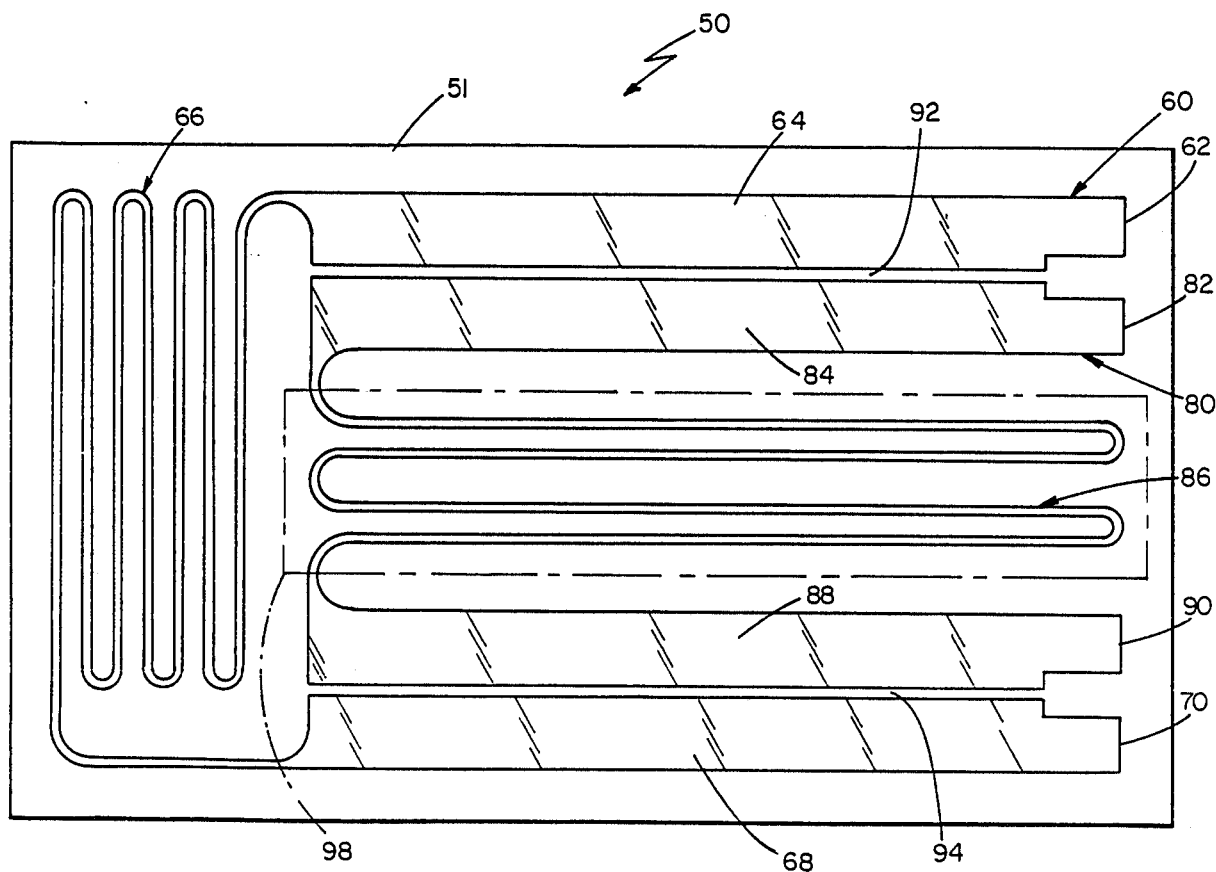
FIG. 2 is a diagram of the pattern of the corrosion sensor of this invention.

Referring to FIG. 2, there is shown the preferred embodiment of the sensor 50 of this invention. The sensor 50 is comprised of two electrodes 60, 80 on a substrate 51. First electrode 60 is the outermost electrode. It has a first terminal 62 connected to a first flat plate 64. The first plate 64 is connected in turn to a long, thin, serpentine section or first choke point 66. (The serpentine nature of the section is for space-saving purposes. The choke point 66 is in turn connected to a second flat plate 68, which also has a second terminal 70. The second electrode 80 is similar. Second electrode 80 begins with a third terminal 82 connected to a third plate 84. Plate 84 is connected to thin, serpentine section or choke point 86, which in turn is connected to fourth plate 88 with its fourth terminal 90. Each electrode 60, 80 has an identical area.

As shown in FIG. 2, plate 64 of the first electrode 60 and plate 84 of the second electrode 80 are separated along their length by a small gap 92 ("the polarization resistance gap"). Similarly, a gap 94 separates plate 68 of the first electrode 60 from plate 88 of the second electrode 80. The gaps 92, 94 are of uniform size, and their specific dimension depends upon the environment in which they are used. In general, they are several times smaller than the separation between the segments of the serpentine portion of an electrode and may be as small as 1 mil.

The preferred method of fabricating the sensor 50 involves photofabrication, which is particularly suited for creating metal electrodes that are very thin. Steel foil, which is flat, smooth and free from buckles, warps, creases or surface rust, is initially cleaned and passivated. It is also treated for adhesion promotion in the usual manner. Any residual rolling oils and surface oxides are removed, and the foil is dried rapidly to prevent re-oxidation.

The cleaned and dried foil is then bonded to a dielectric backing (a glass reinforced epoxy (GRE) panel). The bonding is done with an adhesive such as Bond-ply and is preferrably done at a clamping pressure of 200 psi at a temperature of 350° F. for one hour. The resulting laminate (the backing plus the foil) is then recleaned and coated with an ultraviolet light sensitive material such as photoresist. Kodak KMER is a suitable photoresist. The photoresist is cured for twenty minutes at 90° C.

An enlarged photomask of the desired sensor pattern as shown in FIG. 2, is produced by any suitable means including drafting or photoplotting (or other means), and the mask is photographically reduced to the desired size of the sensor. The exposed film is developed and placed in contact with the laminate. (Actually, a number of sensor patterns will be produced on the same film.) A vacuum draw-down is used to assure unifrom contact of the film with the laminate. It is then exposed to an ultraviolet light source for a preselected time (usually fifteen seconds to two minutes, depending upon light intensity), and this creates a latent image on the foil. The places for the electrodes are masked by the film so as not to be exposed to the ultraviolet light. As a result, they remain coated with unexposed photoresist. The remainder of the foil which is exposed to the light is coated with photoresist that has been exposed. The usual developer solution for the particular photoresist used is then applied, and it removes the photoresist that has been exposed to the ultraviolet light.

The laminate is then placed in an etching solution such as ferric chloride (having a density of 46 Baume at a temperature of 120° F.). This will etch away the unprotected foil, leaving the foil covered with the unexposed photoresist in the form of the desired electrode pattern. The unexposed photoresist is then removed from the electrode pattern by a stripping solution. The resulting sensor is then attached to a flexible, self-adhesive backing or to a rigid self-supporting backing or substrate. In the preferred embodiment, the second choke point 86 of the inside electrode 80 is then covered with a layer 98 to protect it from the environment.

Because of this method of fabrication, the sensor 50 can be made in large quantities and very inexpensively, without the need for individual calibration of each one. Also, the gaps between the flat plates of the sensor electrodes can be made very small, which allows the sensor to be used to measure environments with high resistivity.

Operation

Referring to FIG. 2, the sensor 50 is operated in the following manner. First, the sensor 50 is placed in the location to be measured so that the electrodes 60, 80 (except for the choke point 86 which is covered) are exposed to the environment in question. Once exposed to the environment in question, the electrodes 60, 80 begin to corrode.

To measure the time averaged corrosion rate using the ER method, the end-to-end electrical resistance of electrode 60 is periodically measured. (This is not measured by means of electrode 80, because its choke point 86 is protected from the environment and will not corrode.) The measurement is accomplished by connecting the terminals 62, 70 to different terminals of the electrical source (not shown in this embodiment, but shown in simplified form in FIG. 1). A small current then runs through the electrode 60 from end to end. (This provides a check of electrical continuity of the electrode 60).

Since the electrical resistance of choke point 66 is much higher than the resistance of the remaining parts of the electrode 60, particularly that of the plates 64, 68, the measured resistance of the overall electrode 60 from end to end will be almost equal to the resistance of choke point 66. In effect, plates 64, 68 act as lead wires to choke point 66.

As the corrosion continues, it reduces the thickness and width of the entire exposed portion of the electrode 60. This has the most effect upon the thin choke point 66, and as a result, over time, the electrical resistance of choke point 66 will increase. This increase is proportional to the amount of corrosion that has occurred. Thus, by means of this ER method, the time averaged corrosion rate can be determined. To make sure this measurement is as accurate as possible, as a reference, the current is also measured through the second electrode 80 with its shielded choke point 86, which helps remove the effect of temperature on the actual measurement.

As for the instantaneous corrosion rate, the terminals of each electrode are connected together and connected to a different terminal of an electrical source (not shown in FIG. 2). Because of the high resistance of the respective choke points 66, 86, little current will flow through them. Instead, a current will flow between the pairs of plates 64, 84 and 68, 88. This current, as previously mentioned, is used to determine the instantaneous corrosion rate.

In addition, however, it may also be used to check the time averaged corrosion rate. If the instantaneous corrosion rate determined using the LPR method is integrated over time, the result is a time averaged measurement. This can be accomplished using mercury coulomb meter (not shown). The electrical current passing through the meter causes mercury to move in a glass tube. The movement is indicative of the current which has passed through the meter and which is equal to the integral of the instantaneous rate over the same time period. The total movement is, therefore, directly proportional to the time averaged rate.

The sensor 50 of this invention has another advantage. The ER method determines total metal loss from all causes. This includes aqueous corrosion as well as mechanical erosion. The integrated LPR method, however, only reveals total metal loss due to aqueous corrosion. Thus, by subtracting the loss determined using the integrated LPR method from the total loss determined using the ER method, the loss due solely to mechanical erosion can be found.

Other Embodiments

Figure 3:
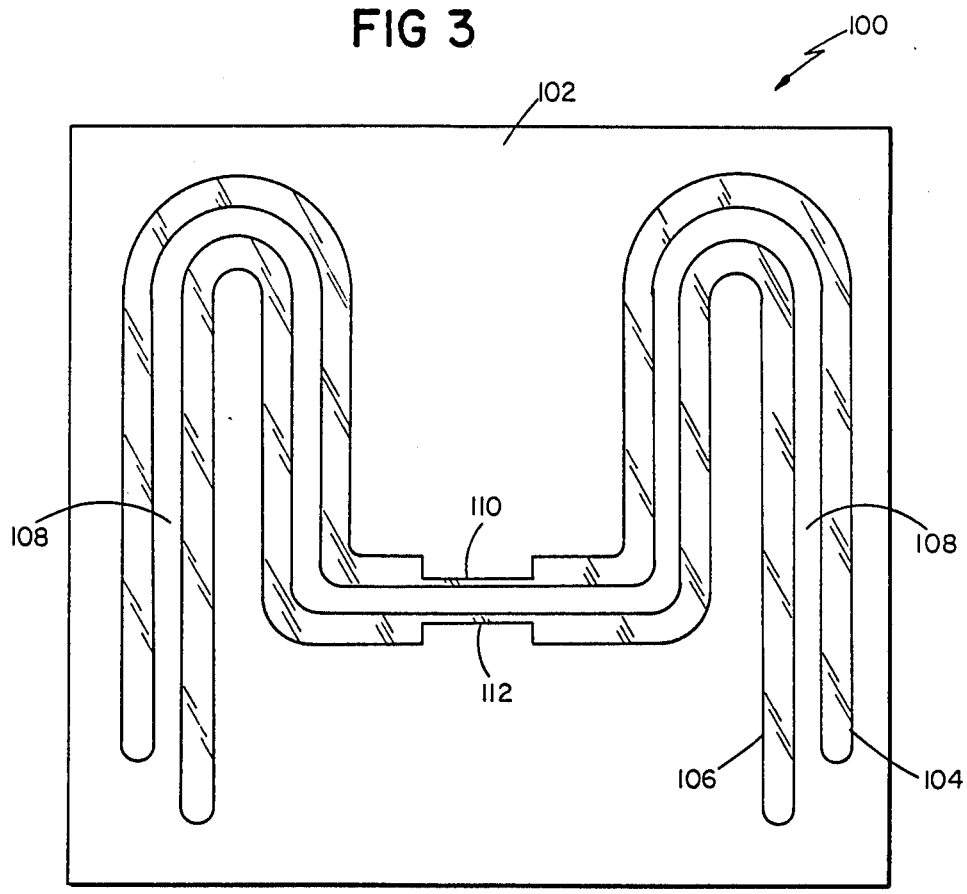
FIG. 3 is a diagram of another sensor of this invention.

Another embodiment of the invention is shown in FIG. 3. There a sensor 100 is comprised of a substrate 102 with a pair of electrodes 104, 106. The electrodes 104, 106 are applied to the substrate 102 in the manner described earlier. The electrodes 104, 106 are separated by a gap 108, and both electrodes have choke points 110, 112, where their width is substantially reduced (and their resistance substantially increased). The operation of the sensor 100 is as described before.

Figure 4:
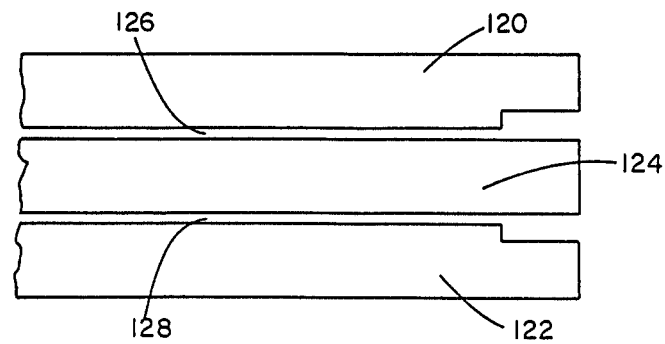
FIG. 4 is a cut-away view of a portion of another electrode arrangement of this invention.

Another variation is shown in FIG. 4. There, the two basic plates 120, 122 (as in FIG. 2) are separated by the third electrode plate 124. There are the usual gaps 126, 128 between the respective plates. The three electrodes are a middle counter electrode, a working electrode and a reference electrode. This arrangement is primarily for environments with higher resistivity, which would require a more significant voltage in order to obtain the required current flow between the plates. A potentiostat (not shown) can be used to drive this embodiment, which involves placing a larger voltage on the counter electrode and using the voltage change between the working and reference electrodes.

Finally, as to this last embodiment, different metals may be used for the electrodes. For example, a noble metal may be used for the counter electrode on which the high voltage is applied to prevent it from breaking down. Also, the reference electrode may be of silver with a chloride surface. Other metals may be used as well.

Other variations will occur to those skilled in the art. What we claim is:

1. A sensor measuring both the corrosion loss and the instantaneous corrosion rate comprising:
    a first electrode having a plate, said first electrode plate being flat and being sufficiently wide so as to have little electrical resistance, said first electrode plate being electrically connected in series to an electrical choke section comprising an elongated conductive portion of substantially narrower width than said plate so as to have a higher electrical resistance,
    a pair of first electrical terminals, one such terminal being connected to said first electrode plate and the other said terminal being connected to said first electrode choke section, said terminals being connected to said first electrode plate and said first electrode choke section so that a voltage applied across said terminals causes a current to flow from one said terminal to the other through at least most of said first electrode plate and said first electrode choke section,
    said first electrode plate and said first electrode choke section being adapted to be exposed to a corrosive environment to be measured,
    a second electrode having a plate, said second electrode plate having the same dimensions as said first electrode plate and having little electrical resistance, said second electrode plate being disposed adjacent to said first electrode plate so as to create a narrow gap therebetween, said gap extending a substantial portion of the lengths of said first electrode plate and said second electrode plate,
    said second electrode plate being adapted to be exposed to the corrosive environment to be measured,
    a pair of second electrode terminals connected to said second electrode plate so that current can flow through said second electrode plate, said second electrode and said second electrode terminals being electrically separate from said first electrode and its said terminals, whereby the amount of corrosion may be determined by using said first electrode terminals to cause current to flow through the first electrode choke section exposed to the corrosive environment and the instantaneous corrosion rate may be determined by using both pairs of terminals and measuring a voltage said gap between the respective electrode plates.

2. The sensor of claim 1 wherein said first electrode has a third section comprising a flat plate, said third section being of the same general dimensions as the said first electrode plate.

3. The sensor of claim 2 wherein said third section is electrically connected in series with said first electrode choke section and said first electrode plate.

4. The sensor of claim 2 wherein said second electrode has a fourth section comprising a flat plate, said fourth section being separated from said third section by a small gap.

5. The sensor of claim 2 wherein each said choke section comprises a serpentine portion.

6. The sensor of claim 2 wherein said sensor has a third electrode disposed between said first and second electrodes.

7. The sensor of claim 2 wherein said second electrode has a second electrode choke section of the same dimensions as said choke section of said first electrode, said second electrode choke section being shielded from the corrosive environment.

* * * * *